United States Patent [19]

Yokoyama et al.

[11] Patent Number: 4,915,931
[45] Date of Patent: Apr. 10, 1990

[54] TC-99M MONONUCLIDE COMPLEX COMPOUND

[75] Inventors: Akira Yokoyama, Otsu; Yasushi Arano, Uji, both of Japan

[73] Assignee: Nihon Medi-Physics Co., Ltd., Hyogo, Japan

[21] Appl. No.: 297,385

[22] Filed: Jan. 17, 1989

[30] Foreign Application Priority Data

Jan. 18, 1988 [JP] Japan .................... 63-8056

[51] Int. Cl.$^4$ .................... A61K 43/00; A61K 49/02; C07F 13/00; C07C 159/00
[52] U.S. Cl. .................... 424/1.1; 534/10; 534/14; 424/DIG. 6
[58] Field of Search .................... 534/14, 10; 424/1.1

[56] References Cited

U.S. PATENT DOCUMENTS

| | | | |
|---|---|---|---|
| 4,287,362 | 9/1981 | Yokoyama et al. | 534/14 X |
| 4,338,248 | 7/1982 | Yokoyama et al. | 424/1.1 X |
| 4,444,743 | 4/1984 | Yokoyama et al. | 424/1.1 |
| 4,511,550 | 4/1985 | Yokoyama et al. | 424/1.1 |
| 4,559,221 | 12/1985 | Arano et al. | 424/1.1 |
| 4,564,472 | 1/1986 | Ueda et al. | 424/1.1 X |
| 4,666,697 | 5/1987 | Takahashi et al. | 424/1.1 |

OTHER PUBLICATIONS

Hositani, T., et al., Int. J. Nucl. Med. Biol., vol. 12, No. 6, pp. 431–437, (1986).
Kramer, A. V., et al., Journal of Labelled Compounds and Radiopharmaceuticals, vol. XIX, Nos. 11–12, pp. 1598–1599, (1982).
Kung, H. F., et al., The Journal of Nuclear Medicine, vol. 25, No. 3, pp. 326–332, (1984).
The Japanese Journal of Nuclear Medicine, vol. 24, No. 8, cover page, contents page, pp. 46, 1194, 1302, (8/20/87).

Primary Examiner—Brooks H. Hunt
Assistant Examiner—Virginia B. Caress

[57] ABSTRACT

A Tc-99m mononuclide complex compound of the formula:

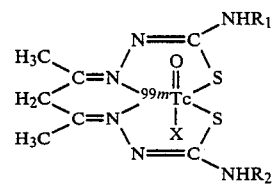

wherein $R_1$ and $R_2$ are each a hydrogen atom or a $C_1$–$C_3$ alkyl group and X is an anion, which is useful as a radioactive diagnostic agent for imaging of brain, cardiac muscle, pancreas or the like.

4 Claims, No Drawings

TC-99M MONONUCLIDE COMPLEX COMPOUND

The present invention relates to a technetium-99m mononuclide complex compound useful as a radioactive diagnostic agent. More particularly, it relates to a highly lipophilic Tc-99m mononuclide complex compound useful as a radioactive diagnostic agent for imaging of brain, cardiac muscle, pancreas or the like.

In the field of nuclear medicine for the purpose of imaging of specific organs and tissues, detection of certain diseases, examination of dynamic behaviors, etc., technetium-99m (hereinafter referred to as "Tc-99m") is widely used as a nuclide, because it has an appropriate half-life (i.e. about 6 hours) and emits an energy of gamma rays (i.e. about 140 KeV) suitable for scintigraphy. Advantageously, Tc-99m is nowadays available at a low cost as the result of development of a Tc-99m generator.

Tc-99m is obtainable from a generator as pertechnetate ion ($TcO_4^-$) having an atomic valency of 7+ in the form of a physiological saline solution. However, pertechnetate ion per se can hardly form a complex compound, and it is necessary to be treated with a ligand under the reductive condition for formation of a complex compound. For instance, pertechnetate ion is admixed with a ligand in the presence of a reducing agent (e.g. stannous salt), whereby Tc-99m is first reduced to a lower atomic valency (3+, 4+ or 5+) and then combined with the ligand to make a complex compound, which is utilized as a radioactive diagnostic agent. Conventional Tc-99m labeled complex compounds admitted as in vivo diagnostic agents by the Japanese Government are all positive or negative in electric charge, and these charged complex compounds are known not to permeate freely through a brain-blood barrier or a cell membrane of cardiac muscle, pancreas or the like.

For imaging of brain, cardiac muscle, pancreas or the like, there are used compounds labeled with a positron emitting nuclide (e.g. C-11, 0-15, F-18) or I-123. However, production of those labeled compounds requires a ultra compact-in house cyclotron or the use of expensive I-123 so that this technique is not widely applicable. Because of this reason, there has been a strong demand on the development of a radioactive diagnostic agent comprising a nuclide which is readily available at a low cost and can afford diagnostic information of a high level like said positron emitting nuclide or I-123. From this viewpoint, recent studies are rather focused on production of neutral Tc-99m mononuclide complex compounds instead of said electrically charged Tc-99m complex compounds.

There are known some bifunctional radioactive medicines, which are characteristic in comprising a bifunctional chelating compound and a radioactive metal bonded thereto through a chelate bond (JP-A-56-34643, JP-A-57-102820, JP-A-59-44328, JP-A-59-44329, JP-A-59-193833). Attempt was made to develop such technique to produce neutral Tc-99m mononuclide complex compounds, which would have high stability and good lipophilic property.

As a result of the extensive study, it has now been found that a complex compound formed between a pentane-2,4-dione-bis(N-substituted or unsubstituted thiosemicarbazone) and Tc-99m bonded thereto through a chelate bond shows high stability and good liphphilic property so that it is useful as a radioactive diagnostic agent for imaging of brain, cardiac muscle, pancreas or the like. This invention is based on the above finding.

The Tc-99m labeled complex compound of this invention is representable by the formula:

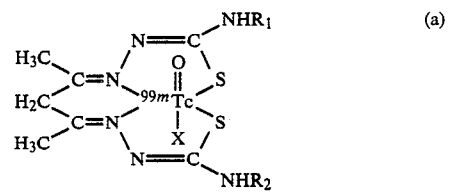 (a)

wherein $R_1$ and $R_2$ are each a hydrogen atom or a $C_1$-$C_3$ alkyl group and X is an anion (e.g. $OH^-$, $Cl^-$, $Br^-$) This complex compound (a) takes a 5,6,5-condensed ring structure and shows higher stability and better lipophilic property than a conventional Tc-99m labeled complex compound of the formula:

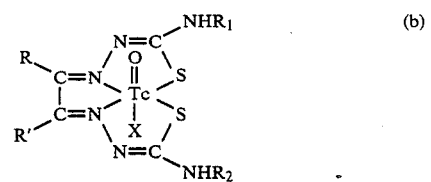 (b)

wherein R is $CH_3CH(OC_2H_5)-$, $HOOCCH_2-$, $(CH_3)_2N(CH_2)_2-$ or the like, R' is a hydrogen atom or a methyl group, $R_1$ and $R_2$ are each a hydrogen atom or a $C_1$-$C_3$ alkyl group and X is an anion such as $OH^-$, $Cl^-$ or $Br^-$, which takes a 5,5,5-condensed ring structure. The ligand in the complex compound (a) is a pentane-2,4-dione-bis(N-substituted or unsubstituted thiosemicarbazone) of the formula:

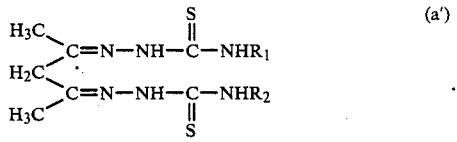 (a')

which is known and can be produced by reacting diazepine or its precursor with thiosemicarbazide (J.Chem.-Soc., (c) 2400–2402 (1967)). In this invention, the pentane-2,4-dione-bis(N-substituted or unsubstituted thiosemicarbazone) (a') as the ligand may be the one produced by said known procedure. But, it can be produced more advantageously in a single step by reacting acetylacetone with an N-substituted or unsubstituted thiosemicarbazide in the presence cf ethylenediamine in aqueous alkanol (e.g. 50% methanol) while refluxing methanol in the presence of ethylenediamine.

The Tc-99m labeled complex compound (a) according to this invention may be produced, for instance, by reacting the pentane-2,4-dione bis(N-substituted or unsubstituted thiosemicarbazone) (a') with Tc-99a' pertechnetate in the presence of stannous chloride as a reducing agent in a phosphate buffer containing sodium tartrate (pH, about 8). When desired, the unreacted pertechnetate may be removed from the reaction mixture by a per se conventional post-treatment procedure such as HPLC (high performance liquid chromatography).

The thus obtained Tc-99m labeled complex compound is useful as an in vivo imaging agent. More specifically, it can be used as an imaging agent in diagnosis of the brain, cardiac muscle, pancreas or the like of mammals including human beings. For the diagnostic purpose, an aqueous solution comprising the Tc-99m labeled complex compound may be administered intravenously. The amount to be administered may be such as giving a radioactivity sufficient for imaging suitable for measurement by a measuring device and is greatly dependent upon the body weight of the patient and the kind of the measuring device. In case of human beings, an appropriate radioactivity to be given is usually within a range of about 5 to 30 mCi.

The present invention will be explained more in detail by the following examples wherein % is by weight unless otherwise indicated.

EXAMPLE 1

Manufacture of Tc-99m-labeled pentane-2,4-dione-bis(N-methylthiosemicabazone) complex compound:

(1) Preparation of pentane-2,4-dione-bis(N-methylthiosemicabazone):

Acetylacetone (10.3 ml; 100 mmol) and ethylenediamine (7.35 ml; 110 mmol) were mixed with 50% aqueous methanol (500 ml), and N-thiosemicarbazide (23.1 g; 220 mmol) was dissolved therein. The resultant solution was heated up to reflux for 8 hours, followed by cooling. The precipitated crystals were collected and recrystallized from methanol to give pentane-2,4-dione-bis(N-methylthiosemicarbazone) (9.88 g; yield, 36.0%).

(2) Preparation of Tc-99m-labeled pentane-2,4-dione-bis(N-methylthiosemicarbazone) complex compound:

Pentane-2,4-dione-bis(N-methylthiosemicarbazone) was dissolved in a phosphate buffer solution (containing 10% ethanol; pH, 8.0) after removal of dissolved oxygen therefrom to make a $1 \times 10^{-3}$ M solution, which was then incorporated with sodium tartrate to make its $1 \times 10^{-1}$ M concentration. To the above prepared solution (1 ml), a $2.2 \times 10^{-2}$ M $SnCl_2$/0.1 M HCl solution (0.01 ml) and a sodium pertechnetate (Tc-99m) solution (10 mCi; 0.5 ml) were added, and the resultant mixture was bubbled with nitrogen at room temperature for about 10 minutes to remove dissolved oxygen, followed by heating at 85° C. for about 30 minutes. The reaction mixture was extracted with hexane for purification and dissolved in physiological saline solution to give a $^{99m}$Tc-labeled pentane-2,4-dione-bis(N-methylthiosemicabazone) complex compound (hereinafter referred to as "$^{99m}$Tc-PETS") solution.

EXAMPLE 2

Radiochemical purity of $^{99m}$Tc-PETS (1):

The $^{99m}$Tc-PETS solution obtained in Example 1 was subjected to thin layer chromatography (TLC) using acetone as a developing solvent. As the result, a single radioactive peak was detected around Rf=0.5, but no other radioactive peak was detected. The radiochemical purity of $^{99m}$Tc-PETS was thus almost 100%, because the Rf values of pertechnetate ion and insoluble technetium oxide as the hydrolyzed product in the above chromatographic system were respectively 0.96 and 0.00.

EXAMPLE 3

Radiochemical purity of $^{99m}$Tc-PETS (2):

The $^{99m}$Tc-PETS solution obtained in Example 1 was subjected to HPLC under the following conditions:

Column: $C_{18}$ column (Cosmosil $C_{18}$, 4.6×150 mm);
Eluting solvent: acetonitrile:0.005 M phosphate buffer (pH, 6.5)=9:2;
Flow rate: 1 ml/min.

As the result, a single radioactive peak was found at the retention time of 3.2 minutes but no other radioactive peak was found. The radiochemical purity of $^{99m}$Tc-PETS was thus almost 100%.

EXAMPLE 4

Lipophilic property of $^{99m}$Tc-PETS:

Distribution ratio of $^{99m}$Tc-PETS as obtained in Example 1 into octanol and buffer was compared with that of the conventional 5,5,5-condensed ring structure complex compound, e.g. technetium-99m-labeled ketoxale-bis-thiosemicarbazone (hereinafter referred to as "$^{99m}$Tc-KTS"). The distribution ratio was determined as follows:

The $^{99m}$Tc-PETS or $^{99m}$Tc-KTS solution (20 μl) was added to a mixture of 0.06 M phosphate buffer (pH, 7.0) (3 ml) and n-octanol (3 ml) and stirred for 30 minutes. After incubation at 37° C. for 15 minutes, the reaction mixture was allowed to stand at room temperature for 30 minutes. Each 0.1 ml was taken from the aqueous layer and the organic layer of the the reaction mixture and subjected to measurement of its radioactivity, and the ratio of the radioactivities thus measured was taken as the octanol/buffer distribution ratio.

At pH 7, the distribution ratio of $^{99m}$Tc-KTS was 2.56, whereas that of $^{99m}$Tc-PETS was 191.3. The lipophilic property of $^{99m}$Tc-PETS is thus much higher than that of $^{99m}$Tc-KTS.

EXAMPLE 5

Body distribution of $^{99m}$Tc-PETS in mouse:

The $^{99m}$Tc-PETS solution as obtained in Example 1 was injected into mice through the tail vein in an amount of 0.1 ml/animal. The mice were sacrificed at pre-determined times after the injection. The radioactivities and weights of various organs and blood taken from the sacrificed mice were measured, and the remaining percentages per gram of each organ were determined. The results are shown in Table 1 wherein the relative ratio of each organ to blood was also shown therein.

TABLE 1

Body Distribution of $^{99m}$Tc-PETS in Mouse (%/g organ)

| Organ | Time elapsed (min) | | | | | |
|---|---|---|---|---|---|---|
| | 0.5 | 2 | 5 | 7 | 15 | 30 |
| Blood | 4.31 | 3.21 | 2.34 | 1.21 | 1.46 | 3.27 |
| Intestine | 2.60 | 3.17 | 3.65 | 2.96 | 4.63 | 7.68 |
| Brain | 4.68 | 4.16 | 2.93 | 1.85 | 0.97 | 0.63 |
| Heart | 15.60 | 6.31 | 4.08 | 2.41 | 1.76 | 2.01 |
| Lung | 11.80 | 8.18 | 3.95 | 2.87 | 2.56 | 3.20 |
| Stomach | 1.95 | 2.66 | 1.97 | 1.63 | 1.50 | 2.31 |
| Spleen | 2.20 | 3.24 | 3.72 | 3.06 | 1.98 | 2.85 |
| Pancreas | 7.11 | 7.32 | 4.30 | 3.18 | 2.19 | 2.05 |
| Liver | 4.83 | 11.70 | 20.10 | 19.10 | 21.90 | 31.70 |
| Kidney | 15.30 | 10.90 | 6.20 | 5.03 | 4.40 | 5.06 |
| Brain/blood | 1.09 | 1.30 | 1.37 | 1.67 | 0.68 | 0.19 |
| heart/blood | 3.52 | 2.17 | 1.88 | 2.16 | 1.21 | 0.62 |
| Pancreas/blood | 1.60 | 2.29 | 1.86 | 2.66 | 1.52 | 0.69 |

As shown in Table 1, $^{99m}$Tc-PETS is rapidly distributed to brain, heart and pancreas after administration, and the distribution ratios of brain/blood, heart/blood and pancreas/blood after 7 minutes from the administration are 1.67, 2.16 and 2.66 (%/g), respectively. This rapid distribution of $^{99m}$Tc-PETS may be attributed to its high stability and lipophilic property in the body. The Tc-99m labeled complex compound of the invention is thus highly effective in imaging of the organs, particularly brain, cardiac muscle and pancrease.

EXAMPLE 6

Preparation of a radioactive diagnostic agent:

As in Example 1, sodium pertechnetate (Tc-99m) (50 mCi) was reacted with pentane-2,4-dione-bis(N-methylthiosemicarbazone) in the presence of stannous chloride in a phosphate buffer solution, and the reaction mixture was shaken with hexane to extract the objective labeled complex compound, i.e. $^{99m}$Tc-PETS The extract was evaporated under sterile conditions, and 0.01 M phosphate buffer-0.15 M sodium chloride solution (2 ml) was added thereto while stirring to make a solution of the labeled complex compound. The solution was filtered through a filter (pore size, 0.22 μm) and charged into a vial to make a radioactive diagnostic agent comprising Tc-99m (20 mCi/vial). When desired, an oxidation inhibitor (e.g. ascorbic acid), a preservative (e.g. benzyl alcohol) or the like may be incorporated into the labeled complex compound solution. The thus prepared diagnostic agent is usually administered intravenously at a dose of about 20 mCi per adult.

What is claimed is:

1. A Tc-99m mononuclide complex compound of the formula:

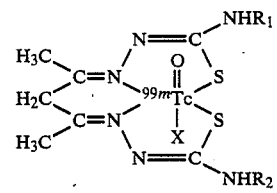

wherein $R_1$ and $R_2$ are each a hydrogen atom or a $C_1$–$C_3$ alkyl group and X is an anion.

2. A method for imaging an organ in a living body, which comprises administering an effective amount of the Tc-99m mononuclide complex compound according to claim 1 to said living body intravenously so that said compound is distributed to and entrained in said organ, and subsequently detecting radiation emitted from said complex compound in said organ.

3. The method according to claim 2, wherein the organ is brain, cardiac muscle or pancreas.

4. The compound of claim 1 wherein $R_1$ and $R_2$ are each methyl.

* * * * *